(12) United States Patent
Zadicario et al.

(10) Patent No.: US 8,425,424 B2
(45) Date of Patent: Apr. 23, 2013

(54) CLOSED-LOOP CLOT LYSIS

(75) Inventors: Eyal Zadicario, Tel Aviv-Yafo (IL); Arik Hananel, Tel Aviv-Yafo (IL); Gilat Schiff, Ra'anana (IL); Javier Grinfeld, Tel Aviv-Yafo (IL)

(73) Assignee: Inightee Ltd., Tirat Carmel (IL)

( * ) Notice: Subject to any disclaimer, the term of this patent is extended or adjusted under 35 U.S.C. 154(b) by 512 days.

(21) Appl. No.: 12/620,235

(22) Filed: Nov. 17, 2009

(65) Prior Publication Data

US 2010/0125193 A1    May 20, 2010

Related U.S. Application Data

(60) Provisional application No. 61/116,111, filed on Nov. 19, 2008.

(51) Int. Cl.
*A61B 8/00* (2006.01)

(52) U.S. Cl.
USPC .......................................................... 600/454

(58) Field of Classification Search .................. 600/439, 600/454
See application file for complete search history.

(56) References Cited

U.S. PATENT DOCUMENTS

| | | | |
|---|---|---|---|
| 2,795,709 A | 6/1957 | Camp | |
| 3,142,035 A | 7/1964 | Harris | |
| 3,942,150 A | 3/1976 | Booth et al. | |
| 3,974,475 A | 8/1976 | Burckhardt et al. | |
| 3,992,693 A | 11/1976 | Martin et al. | |
| 4,000,493 A | 12/1976 | Spaulding et al. | |
| 4,074,564 A | 2/1978 | Anderson | |
| 4,206,653 A | 6/1980 | LeMay | |
| 4,211,132 A | 7/1980 | Nichols, III et al. | |
| 4,339,952 A | 7/1982 | Foster | |
| 4,454,597 A | 6/1984 | Sullivan | |
| 4,478,083 A | 10/1984 | Hassler et al. | |
| 4,505,156 A | 3/1985 | Questo | |
| 4,526,168 A | 7/1985 | Hassler et al. | |
| 4,537,074 A | 8/1985 | Dietz | |
| 4,549,533 A | 10/1985 | Cain et al. | |
| 4,554,925 A | 11/1985 | Young | |
| 4,636,964 A | 1/1987 | Jacobs et al. | |
| 4,662,222 A | 5/1987 | Johnson | |
| 4,817,614 A | 4/1989 | Hassler et al. | |

(Continued)

FOREIGN PATENT DOCUMENTS

| DE | 4345308 C2 | 2/2001 |
|---|---|---|
| EP | 0320303 | 6/1989 |

(Continued)

OTHER PUBLICATIONS

McGough et al., "Direct Computation of Ultrasound Phased-Array Driving Signals from a Specified Temperature Distribution for Hyperthermia," IEEE Transactions on Biomedical Engineering, vol. 39, No. 8, pp. 825-835 (Aug. 1992).

(Continued)

*Primary Examiner* — Brian Casler
*Assistant Examiner* — Saurel J Selkin
(74) *Attorney, Agent, or Firm* — Bingham McCutchen LLP

(57) ABSTRACT

The present invention provides procedures and systems that use a closed-loop approach for directing ultrasound energy at a clot while monitoring blood flow and/or liquification of the clot tissue so as to allow automated and/or manual adjustments to various treatment parameters.

6 Claims, 2 Drawing Sheets

U.S. PATENT DOCUMENTS

| | | |
|---|---|---|
| 4,858,597 A | 8/1989 | Kurtze et al. |
| 4,865,042 A | 9/1989 | Umemura et al. |
| 4,888,746 A | 12/1989 | Wurster et al. |
| 4,889,122 A | 12/1989 | Watmough et al. |
| 4,893,284 A | 1/1990 | Magrane |
| 4,893,624 A | 1/1990 | Lele |
| 4,937,767 A | 6/1990 | Reuschel et al. |
| 5,197,475 A | 3/1993 | Antich et al. |
| 5,209,221 A | 5/1993 | Riedlinger |
| 5,211,160 A | 5/1993 | Talish et al. |
| 5,247,935 A | 9/1993 | Cline et al. |
| 5,271,400 A | 12/1993 | Dumoulin et al. |
| 5,275,165 A | 1/1994 | Ettinger et al. |
| 5,291,890 A | 3/1994 | Cline et al. |
| 5,307,812 A | 5/1994 | Hardy et al. |
| 5,307,816 A * | 5/1994 | Hashimoto et al. ............ 600/439 |
| 5,318,025 A | 6/1994 | Dumoulin et al. |
| 5,323,779 A | 6/1994 | Hardy et al. |
| 5,327,884 A | 7/1994 | Hardy et al. |
| 5,329,930 A | 7/1994 | Thomas, III et al. |
| 5,368,031 A | 11/1994 | Cline et al. |
| 5,368,032 A | 11/1994 | Cline et al. |
| 5,379,642 A | 1/1995 | Reckwerdt et al. |
| 5,391,140 A | 2/1995 | Schaetzle et al. |
| 5,413,550 A | 5/1995 | Castel |
| 5,435,312 A | 7/1995 | Spivey et al. |
| 5,443,068 A | 8/1995 | Cline et al. |
| 5,474,071 A | 12/1995 | Chapelon et al. |
| 5,485,839 A | 1/1996 | Aida et al. |
| 5,490,840 A | 2/1996 | Uzgiris et al. |
| 5,507,790 A | 4/1996 | Weiss |
| 5,520,188 A | 5/1996 | Hennige et al. |
| 5,520,612 A | 5/1996 | Winder et al. |
| 5,526,814 A | 6/1996 | Cline et al. |
| 5,549,638 A | 8/1996 | Burdette |
| 5,553,618 A | 9/1996 | Suzuki et al. |
| 5,573,497 A | 11/1996 | Chapelon |
| 5,582,578 A | 12/1996 | Zhong et al. |
| 5,590,653 A | 1/1997 | Aida et al. |
| 5,590,657 A | 1/1997 | Cain et al. |
| 5,601,526 A | 2/1997 | Chapelon et al. |
| 5,605,154 A | 2/1997 | Ries et al. |
| 5,606,971 A | 3/1997 | Sarvazyan |
| 5,617,371 A | 4/1997 | Williams |
| 5,617,857 A | 4/1997 | Chader et al. |
| 5,643,179 A | 7/1997 | Fujimoto |
| 5,662,170 A | 9/1997 | Donovan et al. |
| 5,665,054 A | 9/1997 | Dory |
| 5,666,954 A | 9/1997 | Chapelon et al. |
| 5,676,673 A | 10/1997 | Ferre et al. |
| 5,687,729 A | 11/1997 | Schaetzle |
| 5,694,936 A | 12/1997 | Fujimoto et al. |
| 5,711,300 A | 1/1998 | Schneider et al. |
| 5,722,411 A | 3/1998 | Suzuki et al. |
| 5,728,062 A | 3/1998 | Brisken |
| 5,739,625 A | 4/1998 | Falcus |
| 5,743,863 A | 4/1998 | Chapelon |
| 5,752,515 A | 5/1998 | Jolesz et al. |
| 5,759,162 A | 6/1998 | Oppelt et al. |
| 5,762,616 A | 6/1998 | Talish |
| 5,769,790 A | 6/1998 | Watkins et al. |
| 5,810,008 A | 9/1998 | Dekel et al. |
| 5,810,731 A | 9/1998 | Sarvazyan et al. |
| 5,873,845 A | 2/1999 | Cline et al. |
| 5,897,495 A | 4/1999 | Aida et al. |
| 5,904,659 A | 5/1999 | Duarte et al. |
| 5,938,600 A | 8/1999 | Van Vaals et al. |
| 5,938,608 A | 8/1999 | Bieger et al. |
| 5,947,900 A | 9/1999 | Derbyshire et al. |
| 5,984,881 A | 11/1999 | Ishibashi et al. |
| 6,004,269 A | 12/1999 | Crowley et al. |
| 6,023,636 A | 2/2000 | Wendt et al. |
| 6,042,556 A | 3/2000 | Beach et al. |
| 6,071,239 A | 6/2000 | Cribbs et al. |
| 6,113,559 A | 9/2000 | Klopotek |
| 6,128,522 A | 10/2000 | Acker et al. |
| 6,128,958 A | 10/2000 | Cain |
| 6,135,960 A | 10/2000 | Holmberg |
| 6,193,659 B1 | 2/2001 | Ramamurthy et al. |
| 6,217,530 B1 | 4/2001 | Martin et al. |
| 6,242,915 B1 | 6/2001 | Hurd |
| 6,246,896 B1 | 6/2001 | Dumoulin et al. |
| 6,263,230 B1 | 7/2001 | Haynor et al. |
| 6,267,734 B1 | 7/2001 | Ishibashi et al. |
| 6,289,233 B1 | 9/2001 | Dumoulin et al. |
| 6,309,355 B1 | 10/2001 | Cain et al. |
| 6,317,619 B1 | 11/2001 | Boernert et al. |
| 6,322,527 B1 | 11/2001 | Talish |
| 6,334,846 B1 | 1/2002 | Ishibashi et al. |
| 6,374,132 B1 | 4/2002 | Acker et al. |
| 6,392,330 B1 | 5/2002 | Zloter et al. |
| 6,397,094 B1 | 5/2002 | Ludeke et al. |
| 6,413,216 B1 | 7/2002 | Cain et al. |
| 6,419,648 B1 | 7/2002 | Vitek et al. |
| 6,424,597 B1 | 7/2002 | Bolomey et al. |
| 6,425,867 B1 | 7/2002 | Vaezy et al. |
| 6,428,532 B1 | 8/2002 | Doukas et al. |
| 6,433,464 B2 | 8/2002 | Jones |
| 6,461,314 B1 | 10/2002 | Pant et al. |
| 6,475,150 B2 | 11/2002 | Haddad |
| 6,478,739 B1 | 11/2002 | Hong |
| 6,506,154 B1 | 1/2003 | Ezion et al. |
| 6,506,171 B1 | 1/2003 | Vitek et al. |
| 6,511,428 B1 | 1/2003 | Azuma et al. |
| 6,522,142 B1 | 2/2003 | Freundlich |
| 6,523,272 B1 | 2/2003 | Morales |
| 6,524,251 B2 | 2/2003 | Rabiner et al. |
| 6,559,644 B2 | 5/2003 | Froundlich et al. |
| 6,566,878 B1 | 5/2003 | Komura et al. |
| 6,582,381 B1 | 6/2003 | Yehezkeli et al. |
| 6,599,256 B1 | 7/2003 | Acker et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,618,608 B1 | 9/2003 | Watkins et al. |
| 6,618,620 B1 | 9/2003 | Freundlich et al. |
| 6,626,854 B2 | 9/2003 | Friedman et al. |
| 6,626,855 B1 | 9/2003 | Weng et al. |
| 6,629,929 B1 | 10/2003 | Jago et al. |
| 6,645,162 B2 | 11/2003 | Friedman et al. |
| 6,652,461 B1 | 11/2003 | Levkovitz |
| 6,666,833 B1 | 12/2003 | Friedman et al. |
| 6,676,601 B1 | 1/2004 | Lacoste et al. |
| 6,676,602 B1 | 1/2004 | Barnes et al. |
| 6,679,855 B2 | 1/2004 | Horn et al. |
| 6,705,994 B2 | 3/2004 | Vortman et al. |
| 6,719,694 B2 | 4/2004 | Weng et al. |
| 6,733,450 B1 | 5/2004 | Alexandrov et al. |
| 6,735,461 B2 | 5/2004 | Vitek et al. |
| 6,761,691 B2 | 7/2004 | Tsuzuki |
| 6,770,031 B2 | 8/2004 | Hynynen et al. |
| 6,770,039 B2 | 8/2004 | Zhong et al. |
| 6,788,619 B2 | 9/2004 | Calvert |
| 6,790,180 B2 | 9/2004 | Vitek |
| 6,824,516 B2 | 11/2004 | Batten et al. |
| 6,951,540 B2 | 10/2005 | Ebbini et al. |
| 6,961,606 B2 | 11/2005 | DeSilets et al. |
| 7,001,379 B2 | 2/2006 | Behl et al. |
| 7,077,820 B1 | 7/2006 | Kadziauskas et al. |
| 7,094,205 B2 | 8/2006 | Marmarelis |
| 7,128,711 B2 | 10/2006 | Medan et al. |
| 7,155,271 B2 | 12/2006 | Halperin et al. |
| 7,175,596 B2 | 2/2007 | Vitek et al. |
| 7,175,599 B2 | 2/2007 | Hynynen et al. |
| 7,264,592 B2 | 9/2007 | Shehada |
| 7,264,597 B2 | 9/2007 | Cathignol |
| 7,267,650 B2 | 9/2007 | Chow et al. |
| 7,344,509 B2 | 3/2008 | Hynynen et al. |
| 7,377,900 B2 | 5/2008 | Vitek et al. |
| 7,429,248 B1 | 9/2008 | Winder et al. |
| 7,452,357 B2 | 11/2008 | Vlegele et al. |
| 7,505,805 B2 | 3/2009 | Kuroda |
| 7,505,808 B2 | 3/2009 | Anderson et al. |
| 7,507,213 B2 | 3/2009 | Schultheiss et al. |
| 7,510,536 B2 | 3/2009 | Foley et al. |
| 7,511,501 B2 | 3/2009 | Wexler |
| 7,535,794 B2 | 5/2009 | Prus et al. |

| | | | |
|---|---|---|---|
| 7,553,284 B2 | 6/2009 | Vaitekunas | |
| 7,603,162 B2 | 10/2009 | Danz et al. | |
| 7,611,462 B2 | 11/2009 | Vortman et al. | |
| 7,652,410 B2 | 1/2010 | Prus | |
| 7,699,780 B2 | 4/2010 | Vitek et al. | |
| 8,057,408 B2 * | 11/2011 | Cain et al. | 601/2 |
| 8,075,488 B2 * | 12/2011 | Burton | 600/454 |
| 2001/0031922 A1 | 10/2001 | Weng et al. | |
| 2002/0016557 A1 | 2/2002 | Duarte et al. | |
| 2002/0035779 A1 | 3/2002 | Krieg et al. | |
| 2002/0082589 A1 | 6/2002 | Friedman et al. | |
| 2002/0095087 A1 | 7/2002 | Mourad et al. | |
| 2002/0111552 A1 | 8/2002 | Maor et al. | |
| 2002/0161300 A1 | 10/2002 | Hoff et al. | |
| 2002/0188229 A1 | 12/2002 | Ryaby | |
| 2003/0004439 A1 | 1/2003 | Pant et al. | |
| 2003/0060820 A1 | 3/2003 | Maguire et al. | |
| 2003/0187371 A1 | 10/2003 | Vortman et al. | |
| 2004/0030251 A1 | 2/2004 | Ebbini et al. | |
| 2004/0059265 A1 | 3/2004 | Candy et al. | |
| 2004/0068186 A1 | 4/2004 | Ishida et al. | |
| 2004/0122316 A1 | 6/2004 | Satoh | |
| 2004/0122323 A1 | 6/2004 | Vortman et al. | |
| 2004/0143187 A1 | 7/2004 | Biagi et al. | |
| 2004/0210134 A1 | 10/2004 | Hynynen et al. | |
| 2004/0210135 A1 | 10/2004 | Hynynen et al. | |
| 2004/0236253 A1 | 11/2004 | Vortman et al. | |
| 2004/0267126 A1 | 12/2004 | Takeuchi | |
| 2005/0033201 A1 | 2/2005 | Takahashi et al. | |
| 2005/0096542 A1 | 5/2005 | Weng et al. | |
| 2005/0131301 A1 | 6/2005 | Peszynski et al. | |
| 2005/0203444 A1 | 9/2005 | Schonenberger et al. | |
| 2005/0251046 A1 | 11/2005 | Yamamoto et al. | |
| 2006/0052661 A1 | 3/2006 | Gannot et al. | |
| 2006/0052701 A1 | 3/2006 | Carter et al. | |
| 2006/0052706 A1 | 3/2006 | Hynynen et al. | |
| 2006/0058678 A1 | 3/2006 | Vitek et al. | |
| 2006/0106300 A1 | 5/2006 | Seppenwoolde et al. | |
| 2006/0173385 A1 | 8/2006 | Lidgren et al. | |
| 2006/0184034 A1 | 8/2006 | Haim et al. | |
| 2006/0184069 A1 | 8/2006 | Vaitekunas | |
| 2006/0206105 A1 | 9/2006 | Chopra et al. | |
| 2006/0229594 A1 | 10/2006 | Francischelli et al. | |
| 2007/0016039 A1 | 1/2007 | Vortman et al. | |
| 2007/0055140 A1 | 3/2007 | Kuroda | |
| 2007/0066897 A1 | 3/2007 | Sekins et al. | |
| 2007/0098232 A1 | 5/2007 | Matula et al. | |
| 2007/0167781 A1 | 7/2007 | Vortman et al. | |
| 2007/0167798 A1 * | 7/2007 | Cai et al. | 600/458 |
| 2007/0197918 A1 | 8/2007 | Vitek et al. | |
| 2007/0219470 A1 | 9/2007 | Talish et al. | |
| 2007/0239062 A1 | 10/2007 | Chopra et al. | |
| 2007/0276237 A1 | 11/2007 | Li | |
| 2008/0027342 A1 | 1/2008 | Rouw et al. | |
| 2008/0031090 A1 | 2/2008 | Prus et al. | |
| 2008/0033278 A1 | 2/2008 | Assif | |
| 2008/0082026 A1 | 4/2008 | Schmidt et al. | |
| 2008/0108900 A1 | 5/2008 | Lee et al. | |
| 2008/0125660 A1 | 5/2008 | Yao et al. | |
| 2008/0183077 A1 | 7/2008 | Moreau-Gobard et al. | |
| 2008/0228081 A1 | 9/2008 | Becker et al. | |
| 2008/0312642 A1 | 12/2008 | Routh et al. | |
| 2009/0088623 A1 | 4/2009 | Vortman et al. | |
| 2009/0118619 A1 | 5/2009 | Oshiki | |
| 2010/0030076 A1 | 2/2010 | Vortman et al. | |
| 2010/0056962 A1 | 3/2010 | Vortman et al. | |
| 2010/0179425 A1 | 7/2010 | Zadicario | |
| 2010/0268088 A1 | 10/2010 | Prus et al. | |
| 2010/0318002 A1 | 12/2010 | Prus et al. | |
| 2011/0066032 A1 | 3/2011 | Vitek et al. | |
| 2011/0094288 A1 | 4/2011 | Medan et al. | |

FOREIGN PATENT DOCUMENTS

| | | |
|---|---|---|
| EP | 0558029 | 9/1993 |
| EP | 1132054 | 9/2001 |
| EP | 151073 | 11/2005 |
| EP | 1774920 A1 | 4/2007 |
| EP | 1790384 | 5/2007 |
| EP | 1936404 | 6/2008 |
| FR | 2806611 A1 | 9/2001 |
| JP | 7-231895 | 9/1995 |
| JP | 11313833 A | 11/1999 |
| JP | 00/166940 | 6/2000 |
| WO | WO-9100059 A1 | 1/1991 |
| WO | WO-95/14505 | 6/1995 |
| WO | WO-0031614 A1 | 6/2000 |
| WO | WO-0158337 | 8/2001 |
| WO | WO-0166189 A1 | 9/2001 |
| WO | WO-0180709 A2 | 11/2001 |
| WO | WO-02/44753 | 6/2002 |
| WO | WO-02058791 A1 | 8/2002 |
| WO | WO-03/013654 A1 | 2/2003 |
| WO | WO-03097162 A2 | 11/2003 |
| WO | WO-03098232 A2 | 11/2003 |
| WO | WO-2004093686 | 11/2004 |
| WO | WO-2005058029 A2 | 6/2005 |
| WO | WO-2006025001 A1 | 3/2006 |
| WO | WO-2006087649 A1 | 8/2006 |
| WO | WO-2006119572 | 11/2006 |
| WO | WO-2007/051066 | 5/2007 |
| WO | WO-2007073551 A1 | 6/2007 |
| WO | WO-2008039449 | 4/2008 |
| WO | WO-2008050278 A1 | 5/2008 |
| WO | WO-2008075203 A2 | 6/2008 |
| WO | WO-2008119054 A1 | 10/2008 |
| WO | WO-2009055587 A1 | 4/2009 |
| WO | WO-2009/081339 | 7/2009 |
| WO | WO-2009094554 | 7/2009 |

OTHER PUBLICATIONS

McDonnald et al. "Usefulness of MR Imaging-Derived Thermometry and Dosimetry in Determining the Threshold for Tissue Damage INduced by Thermal Surgery in Rabbits," Radiology, vol. 216, No. 2000 pp. 517-523 (2000).

Suprijanto et al. "Displacement Correction Scheme for MR-Guided Interstitial Laser Therapy," Ellis RE, Peters TM (Eds.): MiCCAI, LNCS 2879, pp. 399-407 (2003).

Shmatukha et al. "Correction of Proton Resonance Frequencey Shift Temperature Maps for Magnetic Field Disturbances Caused by Breathing," Physics in Medicine and Biology, vol. 51, No. 18 pp. 4689-4705 (2006).

De Senneville et al., "An Optimised Multi-Baseline Approach for On-Line MR-Temperature Monitoring on Commodity Graphics Hardware," Biomedical Imaging, pp. 1513-1516 (2008).

Vigen et al., "Triggered, Navigated, Multi-Baseline Method for Proton Resonance Frequency Temperature Mapping with Respiratory Motion," Magnetic Resonance in Medicine, vol. 50, pp. 1003-1010 (2003).

Medel, Ricky et al., "Sonothrombolysis: An Emerging Modality for the Management of Stroke", Neurosurgery, vol. 65, No. 5, Nov. 2009, pp. 979-993 (15 pages).

Maxwell AD, "Noninvasive Thrombolysis Using Pulsed Ultrasound Cavitation Therapy—Histotripsy"—Abstract, U.S. National Library of Medicine National Institutes of Health, Ultrasound Med Biol. Oct. 23, 2009 (1 page).

Fronheiser et al., "3D Acoustic Radiation Force Impulse (ARFI) Imaging Using a 2D Matrix Array: Feasibility Study," Ultrasonics Symposium, pp. 1144-1147 (Oct. 2006).

Wu et al., "MRImaging of Shear Waves Generated by Focused Ultrasound," Magnetic Resonance in Medicine, vol. 43, pp. 111-115 (2000).

Heikkila et al., "Simulations of Lesion Detection Using a Combined Phased Array LHMI-Technique,"Ultrasonics, IPC Science and Technology Press Ltd., vol. 48, No. 6-7, pp. 568-573 (Nov. 2008).

Botros et al., "A hybrid computational model for ultrasound phased-array heating in presence of strongly scattering obstacles," IEEE Trans. On Biomed. Eng., vol. 44, No. 11, pp. 1039-1050 (Nov. 1997).

Cain et al., "Concentric-ring and Sector-vortex Phased-array Applicators for Ultrasound Hperthermia," IEEE Trans. On Microwave Theory & Techniques, vol. MTT-34, No. 5, pp. 542-551 (May 1986).

Chen et al., "MR Acoustic Radiation Force Imaging: Comparison of Encoding Gradients."

Cline et al., "Focused US system for MR imaging-guide tumor ablation," Radiology, v. 194, No. 3, pp. 731-738 (Mar. 1995).
Cline et al., "MR Temperature mapping of focused ultrasound surgery," Magnetic Resonance in Medicine, vol. 32, No. 6, pp. 628-636 (1994).
Cline et al., "Simultaneous magnetic resonance phase and magnitude temperature maps in muscle," Magnetic Resonance in Medicine, vol. 35, No. 3, pp. 309-315 (Mar. 1996).
Daum et al., "Design and evaluation of a feedback based phased array system for ultrasound surgery," IEEE Trans. Ultrason. Ferroelec. Freq. Control, vol. 45, No. 2, pp. 431-434 (1998).
de Senneville et al., "Real-time adaptive methods for treatment of mobile organs by MRI-controlled high-intensity focussed Ultrasound," Magnetic Resonance in Medicine 57:319-330 (2007).
Fjield et al, "The Combined Concentric-ring and Sector-vortex Phased Array for MRI Guided Ultrasound Surgery," IEEE Trans. On Ultrasonics, Ferroelectrics and Freq. Cont., vol. 44, No. 5, pp. 1157-1167 (Sep. 1997).
Herbert et al., "Energy-based adaptive focusing of waves: application to ultrasonic transcranial therapy," 8th Intl. Symp. On Therapeutic Ultrasound.
Huber et al., "A New Noninvasive Approach in Breast Cancer Therapy Using Magnetic Resonance Imaging-Guided Focussed Ultrasound Surgery," Cancer Research 61, 8441-8447 (Dec. 2001).
International Preliminary Report on Patentability in International Patent Application No. PCT/IB2004/001512, mailed Dec. 8, 2005.
International Search Report and Written Opinion in International Patent Application No. PCT/IB2004/001498, dated Aug. 31, 2004.
International Search Report and Written Opinion in International Patent Application No. PCT/IB2005/002273, mailed Dec. 20, 2005.
International Search Report and Written Opinion in International Patent Application No. PCT/IB2005/002413, mailed Nov. 22, 2005.
International Search Report and Written Opinion in International Patent Application No. PCT/IB2006/001641, mailed Sep. 25, 2006.
International Search Report and Written Opinion in International Patent Application No. PCT/IB2006/003300, mailed Feb. 14, 2008.
International Search Report and Written Opinion in International Patent Application No. PCT/IB2007/001079, mailed Dec. 10, 2007.
International Search Report and Written Opinion in International Patent Application No. PCT/IB2007/002134, mailed Dec. 13, 2007.
International Search Report and Written Opinion in International Patent Application No. PCT/IB2007/002140, mailed Dec. 29, 2008.
International Search Report and Written Opinion in International Patent Application No. PCT/IB2008/003069, mailed Apr. 27, 2009.
Jolesz et al., "Integration of interventional MRI with computer-assisted surgery," J. Magnetic Resonance Imaging. 12:69-77 (2001).
Kohler et al., "Volumetric HIFU Ablation guided by multiplane MRI thermometry," 8th Intl. Symp. On Therapeutic Ultrasound, edited by E.S. Ebbini, U. of Minn. (Sep. 2009).
Kowalski et al., "Optimization of electromagnetic phased-arrays for hyperthermia via magnetic resonance temperature estimation," IEEE Trans. On Biomed. Eng., vol. 49, No. 11, pp. 1229-1241 (Nov. 2002).
McDannold et al., "MRI evaluation of thermal ablation of tumors and focused ultrasounds," JMRI vol. 8, No. 1, pp. 91-100 (1998).
McDannold et al., "Magnetic resonance acoustic radiation force imaging," Med. Phys. vol. 35, No. 8, pp. 3748-3758 (Aug. 2008).
Mougenot et al., "MR monitoring of the near-field HIFU heating," 8th Intl. Symp. On Therapeutic Ultrasound, edited by E.S. Ebbini, U. of Minn. (Sep. 2009).
Partial International Search Report and Written Opinion in International Patent Application No. PCT/IB2007/001079, dated Sep. 25, 2007.
Vimeux et al., "Real-time control of focused ultrasound heating based on rapid MR thermometry," Investig. Radiology, vol. 43, No. 3, pp. 190-193.
Vykhodtseva et al., "MRI detection of the thermal effects of focused ultrasound on the brain," Ultrasound in Med. & Biol., vol. 26, No. 5, pp. 871-880 (2000).
Written Opinion in International Patent Application No. PCT/IL01/00340, mailed Feb. 24, 2003.
Written Opinion in International Patent Application No. PCT/IL02/00477, mailed Feb. 25, 2003.
Written Opinion in International Patent Application No. PCT/IB03/05551, mailed Sep. 10, 2004.
"How is Ablatherm treatment performed?" http://www.edap-hifu.com/eng/physicians/hifu/3c_treatment_treat-description.htm, accessed Jan. 3, 2003.
"What is HIFU? HIFU: High Intensity Focused Ultrasound," http://www.edap-hifu.com/eng/physicians/hifu2a_hifu_overview.htm, accessed Jan. 3, 2003.
"What are the physical principles?" http://www.edap-hifu.com/eng/physicians/hifu/2c_hifu_physical.htm, accessed Jan. 3, 2003.
"How does HIFU create a lesion?" http://www.edap-hifu.com/eng/physicians/hifu/2d_hifu_lesion.htm, accessed Jan. 3, 2003.
"Prostate Cancer Phase I Clinical Trials Using High Intensity Focused Ultrasound (HIFU)," Focus Surgery, http://www.focus-surgery.com/PCT%20Treatment%20with%2OHIFU.htm, accessed Jan. 3, 2003.
"Abstract" Focus Surgery, http://www.focus-surgery.com/Sanghvi.htm, accessed Jan. 3, 2003.
Exablate 2000 Specification, InSightec, Ltd. (2 pages).
FDA Approves Exablate 2000 as Non-invasive surgery for Fibroids, Oct. 22, 2004.
International Search Report and Written Opinion in International Patent Application No. PCT/IB2010/000189, mailed Jun. 1, 2010.
International Search Report for PCT/IB03/05551 completion date Mar. 2, 2004 (5 pages).
International Search Report and Written Opinion in Internation Patent Application No. PCT/IB2010/000971, mailed Jul. 29, 2010 (9 pages).

* cited by examiner

CLOSED-LOOP CLOT LYSIS

CROSS-REFERENCE TO RELATED APPLICATIONS

This application claims priority to and the benefits of U.S. provisional patent application Ser. No. 61/116,111, filed Nov. 19, 2008, the entire disclosure of which is incorporated be reference herein.

TECHNICAL FIELD

The present invention relates generally to systems and methods for performing noninvasive procedures using acoustic energy, and, more particularly, to systems and methods for focusing ultrasonic energy to treat thrombotic disease.

BACKGROUND INFORMATION

Tissue, such as a benign or malignant tumor or blood clot within a skull or other region of a patient's body may be treated invasively by surgically removing the tissue, or non-invasively by using effects of focused ultrasound. Both approaches may effectively treat certain localized conditions within the brain, but involve delicate procedures in which it is desired to avoid destroying or damaging otherwise healthy tissue. These treatments may not be appropriate for conditions in which diseased tissue is integrated into healthy tissue, unless destroying the healthy tissue is unlikely to affect neurological function significantly.

The application of ultrasound energy, has been investigated as a potential primary and adjunctive treatment for thrombotic disease. High-intensity focused ultrasound (HIFU) has been shown to enhance thrombolysis induced by tissue plasminogen activator (tPA) in-vitro and in-vivo.

Focused ultrasound, has particular appeal for treating tissue within the brain because it generally does not disturb intervening or surrounding healthy tissue. Focused ultrasound may also be attractive because acoustic energy generally penetrates well through soft tissues and ultrasonic energy, in particular, may be focused toward focal zones having a cross-section of only a few millimeters due to relatively short wavelengths (e.g., as small as 1.5 millimeters (mm) in cross-section at one Megahertz (1 MHz)). Thus, ultrasonic energy may be focused at a small target in order to ablate the tissue without significantly damaging surrounding healthy tissue.

To focus ultrasonic energy toward a desired target, drive signals are sent to a piezoelectric transducer having a number of transducer elements such that constructive interference occurs at a "focal zone." At the focal zone, sufficient acoustic energy may be delivered either to heat tissue until necrosis occurs, or mechanically disrupt its structure until the tissue is destroyed. Preferably, tissue along the path through which the acoustic energy passes (the "pass zone") outside the focal zone is heated only minimally, if at all, thereby minimizing damage to tissue outside the focal zone.

Stroke is the third leading cause of death in the United States and a leading cause of adult disability. In general, strokes can be classified as either ischemic or hemorrhagic. In ischemic strokes, the blockage of blood flow results from a clot in intracerebral vessels, whereas hemorrhagic strokes are caused by ruptured blood vessels. Several clinical trials were initiated to evaluate the safety and efficacy of ultrasound-assisted tPA approach to treat stroke patients. However, these trials were generally unsuccessful due to adverse events associated with bleeding that were triggered outside the target area.

Accordingly, there is a need for systems and methods for effectively focusing acoustic energy to treat clots in a manner that does not adversely affect surrounding tissue and can be administered in a timely fashion.

SUMMARY OF THE INVENTION

The present invention provides procedures and systems that facilitate non-invasive, focused clot lysis. In general, the technique uses a closed-loop approach such that immediate feedback is provided to an operator or to an automatic control system. One application directs ultrasound energy at the clot so as to cause it to become smaller (typically through liquefaction) while sparing adjacent tissue. During the application of the ultrasound, blood flow is monitored in the vicinity of the blocked vessel, or, in the case of hemorrhagic stroke, the liquefaction of the clot is monitored. For example, in some embodiments, images are taken of the area surrounding the clot and displayed to an operator so as to provide a real-time indication of blood flow in and/or around the affected blood vessel or the content of the hemorrhage (i.e., solid versus liquid). Based on the monitoring, alterations to the treatment regimen can be administered by increasing or decreasing the overall pressure, energy and changing temporal or spatial characteristics of the acoustic beam (i.e., on/off timing, location). For example the energy transmitted to the clot may be increased or decreased and/or the focus of the ultrasound transducer may be adjusted by modifying various operational parameters of the individual transducer elements. In other embodiments, control is automated—that is, a controller responds to the measured blood flow (and changes therein), and/or the content of the hemorrhage and alters the intensity, pressure and/or direction of the ultrasound energy accordingly. As a result, victims of stroke and other clot-related conditions can be treated in a non-invasive, timely manner.

In a first aspect, a system for delivering acoustic energy to a clot within a blood vessel or a hemorrhage includes a high-intensity focused ultrasound phased-array transducer, means for monitoring blood flow (such as a visual display providing magnetic resonance images, computer tomography images and/or ultrasound images) in the vicinity of the blood vessel as ultrasound energy is directed at the blood vessel, and a controller for operating the transducer and adjusting transducer operation based on the monitored blood flow.

In some embodiments, the system also includes a processor for generating correction factors based on the monitored blood flow, and the controller responds to the processor by implementing the correction factors (and, based thereon, adjusting the application of the acoustic energy). A beam former may also be used to drive the transducer elements according to the correction factors. In certain cases, the controller may also allow an operator to manually override the correction factors. The phased-array transducer may include numerous transducer elements, each of which can deliver ultrasound energy independent of the others. The images may, in some cases, provide an indication of blood flow and/or oxygen level in blood vessels about the clot, and in certain within the specific blood vessel containing the clot. In other instances, the focal quality of the images being used to monitor the blood flow may be used to determine one or more adjustments.

The correction factors may include phase correction factors for each (or a group of) transducer elements. In such cases, the controller may also include a phase adjuster for adjusting the excitation signals provided to the transducer elements based on the correction factors. The controller may include amplifiers coupled to the phase adjuster for amplifying the excitation signals provided to respective transducer elements based upon amplitude and/or phase correction factors. In some embodiments, the processor constructs an acoustic transmission regime that includes a series of treatment parameters optimized to perform clot lysis. In such cases, the correction factors influence the treatment parameters, thereby adjusting the delivery of ultrasound energy to the clot.

In another aspect of the invention, a system for treating a clot within a blood vessel includes a focused ultrasound energy transducer, means for monitoring the liquid content of the blood vessel as energy is delivered to the clot (by an operator using a visual display, for example), and a controller for adjusting the transducer operation based on the monitored liquid content.

In some case cases, the system also includes a processor for generating correction factors based on the liquefaction information. In such cases, the controller is responsive to the processor and implements the correction factors, thereby influencing the application of acoustic energy to the clot.

In another aspect of the invention, a method for treating a clot within a blood vessel includes applying focused ultrasound energy to the blood vessel using a focused ultrasound phased-array transducer, monitoring blood flow in a vicinity of the blood vessel, and operating the transducer including adjusting the transducer operation based on the monitored blood flow.

In some embodiments, the method also includes obtaining subsequent images (e.g., magnetic resonance images, computer tomography images and/or ultrasound images) of the blood vessel during the application of the ultrasound energy and generating correction factors based on the images for transducer elements that comprise the transducer array. In some cases, the focal quality of the images used to monitor the blood flow may also be used to determine or influence the correction factors.

The correction factors are then used to create excitation signals based upon the correction factors to focus acoustic energy from the transducer elements at the clot. In some implementations, the above technique may be repeated until the clot is substantially liquefied. The correction factors may include phase correction factors for each (or a group of) transducer elements. In such cases, the excitation signals may be adjusted based on the correction factors, and may further be amplified prior to being provided to respective transducer elements based upon amplitude correction factors. In some embodiments, an acoustic transmission regime that includes a series of treatment parameters optimized to perform clot lysis may be provided. In such cases, the correction factors influence the treatment parameters, thereby adjusting the delivery of ultrasound energy to the clot.

In another aspect, a method for treating a clot within a blood vessel includes applying focused ultrasound energy to the blood vessel using a focused ultrasound phased-array transducer, monitoring liquid content of the clot in a vicinity of the blood vessel, and operating the transducer including adjusting the transducer operation based on the monitored liquid content.

In some case cases, images may be used to monitor the liquid content of the clot, and correction factors may be determined based on the liquefaction information as provided in the images.

The foregoing and other objects, features and advantages of the present invention disclosed herein, as well as the invention itself, will be more fully understood from the following description of preferred embodiments and claims, when read together with the accompanying drawings.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

Figure 1:
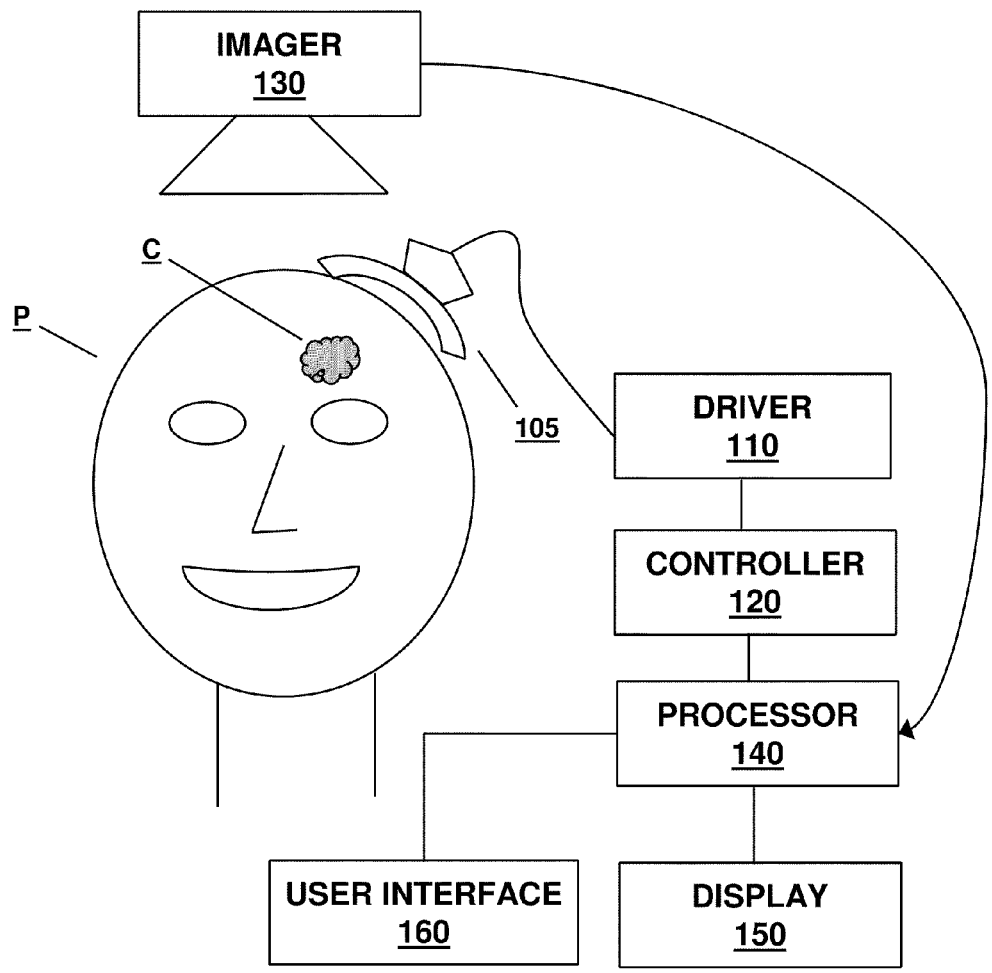
FIG. 1 schematically illustrates a system for monitoring physiological effects of ultrasound treatment in accordance with various embodiments of the invention.

In accordance with the present invention and referring to FIG. 1, a system for quickly treating a patient P suffering from a stroke and/or an intracranial clot C includes a high-intensity focused-ultrasound phased-array transducer 105 (which is driven by one or more drivers 110), a controller 120, and one or more imagers 130 for monitoring clinical parameters related to the clot C. The parameters are detectable via the imaging apparatus 130 and can be used to monitor the successful liquefaction of the clot C. Examples of such parameters include blood flow in the vicinity of a blood vessel being treated and/or liquification of the clot C. In various implementations, the system may also include a processor 140 and a display 150. Optionally, the system may also include a user interface 160, such as a touch screen, a keyboard, and/or a mouse. Preferably, the system is configured for delivering ultrasonic energy between ten kilohertz (0.01 MHz) and ten Megahertz (10 MHz) to tissue within the skull or other anatomical regions. Such a system may be used to treat blood clots lodged within blood vessels of a patient or a clot outside blood vessels (generated by ruptured blood vessels) by delivering acoustic energy to the clot. In some cases, the clot may be partially or completely blocking a blood vessel in the patient's cranium, or applying intra cranial pressure in case of hemorrhagic clot and causing life-threatening conditions such as a stroke. During delivery of the ultrasonic energy, blood flow (as well as other clinical parameters) in and/or around the affected blood vessel is monitored, and adjustments made to one or more treatment parameters based thereon. The adjustments may be automatic or manual. For example, various images of the patient's anatomy surrounding the clot may be viewed on a display, and adjustments made based on automated or human analysis of the images.

The transducer 105 may include "n" (where n>1) transducer elements, thereby providing a multiple-element transducer array. The transducer 105 may include a flexible or semi-rigid base or panel conforming to the shape of patient's anatomy, such as the skull if being used to treat cranial blood clots. The transducer 105 may be pre-curved (e.g. biased to a spherical or other concave shape), such that the transducer may be placed on or near a portion of a skull. Alternatively, the transducer 105 may be planar, parabolic, or any other suitable shape, e.g., circular, elliptical, and the like.

Suitable HIFU phased-array transducers are known in the art. See, e.g., co-pending, commonly-owned U.S. patent application Ser. No. 10/328,584, entitled "Tissue Aberration Corrections in Ultrasound Therapy."

The system may obtain, process and present images of the interior anatomy of the patient P, including the area surrounding the clot C. For example, the images may be taken using a magnetic resonance imaging (MRI) device, a computer tomography (CT) device, or an ultrasound imaging device. The images processed by the processor 140 and presented on the display 150 indicate the state of blood flow and/or liquification of tissue about the clot C, either within the specific blood vessel in which the clot is lodged, or, in some cases, in blood vessels surrounding the clot or a general measure of perfusion surrounding the clot C or within the hemorrhagic clot. As ultrasound energy is applied to the clot, an operator views the images in real-time or pseudo-real time (e.g., a delay of less than five seconds), and thus is able to see the effects of the ultrasound on the clot and the resulting improvement of blood flow or perfusion. The effects of reflow or liquefaction maybe also assessed directly or by other bio-imaging parameters.

Based on the observed and/or detected blood flow or liquid content of the hemorrhage, a processor 140 may generate correction factors to be applied to the signals that drive the transducers 105. The processor 140 may, for example, determine the correction factors by automatically analyzing images and estimating blood flow or liquid content (and, in some embodiments, identifying tissue characteristics of interest) from the images. Sufficient information is provided by the images (or other monitoring modality) to facilitate determination of the correction factors. Alternatively, a user may manually analyze the images and observe blood flow or liquid content and identify tissue characteristics, or a combination of automatic and manual analysis may be used. In some instances, the focal quality of the images themselves may be determined and used to influence the correction factors. For example, if a particular image is know to be of poor quality, its contribution to the correction factor(s) may be down-weighted.

The processor 140 may, for example, receive instructions as input by the operator, or, in some cases, automatically recognize an increase in blood flow, perfusion (or lack thereof), and/or liquid content based, for example, on the images. The correction factors can be applied to treatment parameters that govern the application of HIFU energy, thereby influencing subsequent ultrasound applications. In some implementations, the processor 140 includes a number of amplifiers and/or phase shifters that are coupled in respective sets. The amplifiers provide amplified excitation signals to the transducer elements 105, e.g., via coaxial cables or other connections, which may individually connect the amplifiers and respective transducer elements.

Among other effects, the correction factors allow the acoustic energy transmitted by the transducer elements to be steered such that the "focal zone" (the region in space toward which the acoustic energy is focused) can be moved, along the z axis (i.e., an axis extending orthogonally from the transmission surface of the transducer into the skull) and/or along the x or y axes. The component of each phase-shift factor associated with steering may be computed using known techniques, e.g., using the average speed of sound in the body (possibly adjusted for different tissue types) and the distance from each transducer element to a target site of interest (the intended focal zone within a tissue region).

In addition, in cranial applications, the correction factors may also compensate for phase distortion of the ultrasonic energy transmitted by each transducer element that occurs when the acoustic energy passes through the skull. The component of each correction factor associated with phase distortion may compensate for perturbations and distortions introduced by the bone of the skull, the skin/skull interface, the dura matter/skull interface, by variations in skull thickness or density, and/or by structural considerations such as air-filled or liquid-filled pockets in the skull. The two components that make up the phase-shift factors, i.e., the steering components and the phase-distortion components, are summed to determine the composite phase-shift factors for the respective channels in order to focus ultrasonic energy at a desired location.

In some cases, the processor 140 or the operator may also construct an initial treatment regime describing various treatment parameters (e.g., pressure, temporal structure, frequency, energy, etc.) that creates a sharp focus (e.g., less than 5 mm) of the ultrasound energy, thereby facilitating clot lysis in a targeted manner. In such cases, the correction factors determined during treatment may be applied to the treatment regime in real-time.

The phase-shift factors may, in some cases, be determined by the processor 140 and/or the system image and display computer, which may be coupled to the controller 120 and to an imager 130. Alternatively, the controller 120 itself may include all necessary hardware components and/or software modules to determine the correction factors instead of requiring a separate computer. The system may include one or more software modules, hardware components, firmware, hardwiring, or any combinations of these. For example, the processor may be a general or special purpose digital data processor programmed with software to generate the phase shift factors, which may be transferred to the controller for subsequent transfer to the phase shifters or directly to the phase shifters based upon images shown on the display.

Figure 2:
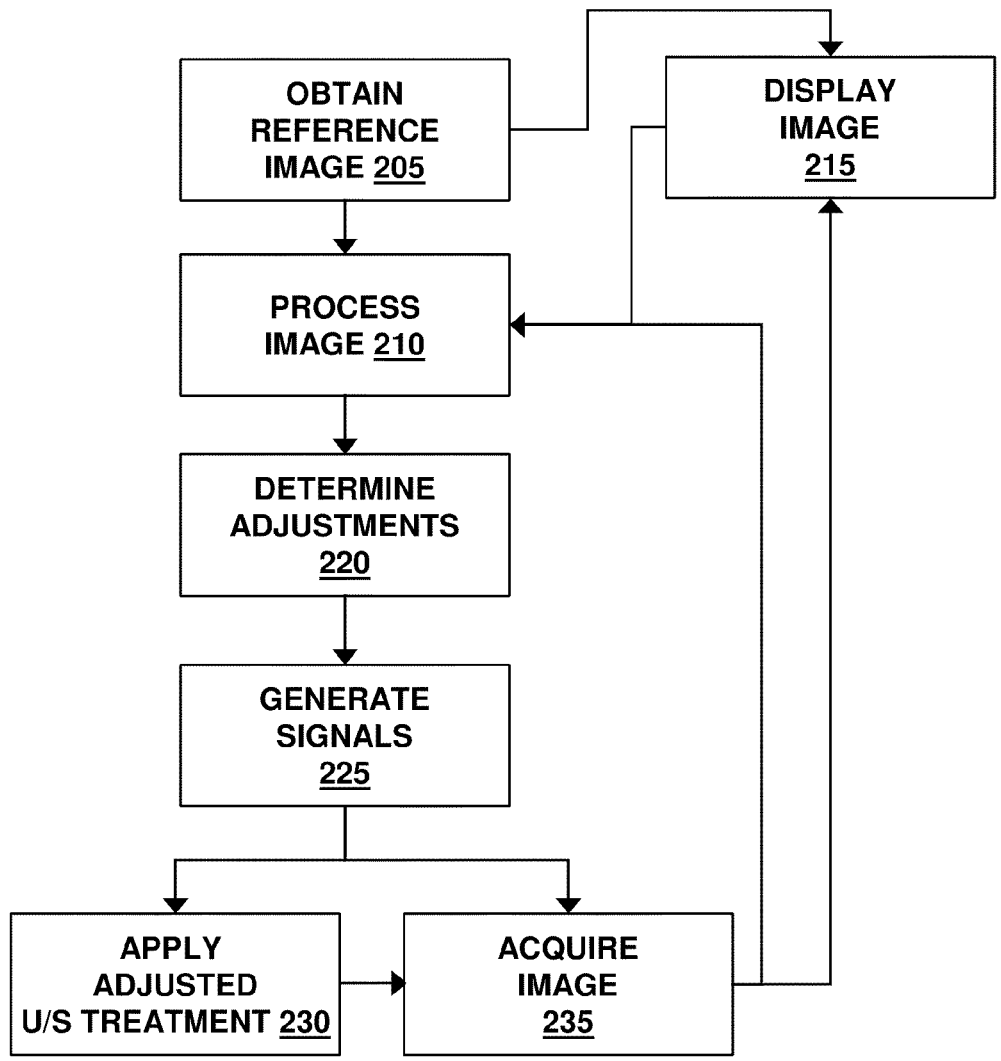
FIG. 2 is a flow chart illustrating a method for administering ultrasound therapy in accordance with various embodiments of the invention.

In addition to providing a system for using high-intensity ultrasound to treat transcranial clots, various embodiments of the invention provide methods for treating stroke victims using such a system as described below and illustrated in FIG. 2.

Upon initial examination, an imager is used to acquire one or more images (STEP 205) of a clot area within a patient's brain. As explained above, the imager may be any of a variety of imaging devices, such as an MRI device, a CT device, or an ultrasound device or a combination/fusion of images.

Data representing the images are transferred to a processor (STEP 210), and presented on a display (STEP 215). In implementations in which the patient is being treated for a stroke, the transfer of image data may occur immediately upon acquiring the images from the patient in order to provide treatment quickly. The transfer may be completed automatically or may occur only upon instruction from a physician or other operator.

Based on the image data, correction factors and other potential adjustments may be determined (STEP 220) for treatment of the clot. As described above, the correction factors may account for different speeds of sound that are encountered as the acoustic energy passes through different tissue types in respective segmented tissue regions. In addition or alternatively, the correction factors may account for aberrations generated by the skull or at boundaries of the segmented tissue regions, as explained further below.

The resulting correction factors, e.g., phase-shift factors and/or amplitude factors, may be used to assist a particular course of treatment, preferably focusing acoustic energy at the clot. Once determined, the correction factors may be provided to the controller which, in turn, provides excitation signals (STEP 225) to the transducer array. The focused ultrasound system uses the correction factors to control a beam former or signal adjuster which delivers excitation or drive signals to the transducer based upon the correction factors for application of the ultrasound treatment (STEP 230). For example, one or more base signals may be supplied to a signal adjuster and split into a plurality of channels, preferably into individual channels corresponding to respective transducer elements or transducer element groupings of the transducer array. The phase of the signals for the respective channels may be adjusted by the signal adjuster according to phase correction factors received by the controller. For example, the phases may be adjusted to compensate for acoustic energy from respective transducer elements passing through different tissue types and/or encountering one or more tissue boundaries. In one particular case, the amplitude adjustments may be done to compensate for a known or calculated skull temperature or to generate desired skull temperature. Such an approach may be implemented a priori based, for example, on an acoustic-bio-heat simulation or based on actual skull temperature measurements. In some cases, the system may assume an even temperature distribution on the skull.

This may be in addition to other phase adjustments that focus the acoustic energy at a particular location or in a particular shape or to compensate for transducer element variations, as is known to those skilled in the art. The phase-adjusted signals may be amplified based upon amplitude correction factors, e.g., by amplifiers, which may amplify the excitation signals. Alternatively, the signals for the respective channels may be amplified before they are phase-adjusted.

The amplified and phase-adjusted excitation signals may be delivered to the transducer to drive the respective transducer elements. The transducer elements convert the excitation signals into acoustic energy that is transmitted from the respective transducer elements of the transducer into the blood vessel containing the clot or hemorrhage inside the brain (or its general area) through any intervening tissue and/or bone, such as the skull.

During the treatment, additional images may be acquired (STEP 235) using the same or a different imager than used to acquire reference image data to monitor the progress of the treatment. For example, the images may be transferred to the processor and/or rendered on a display for real-time or nearly real-time monitoring. In some implementations, the images acquired during treatment may be compared with the previously acquired reference images to determine if, for example, the blood flow within the blood vessel has improved or the hemorrhage has been liquefied. This comparison may be made by the operator or in an automated fashion using image-analysis software configured to recognize fluid flow through or liquid content of a clot. If necessary, the treatment parameters may be adjusted, e.g., by providing further amplitude and/or phase correction factors, to modify the energy delivered to the tissue region and reflect events as they unfold, e.g., to increase monitored blood flow or liquid content. Treatment is thereby delivered in a controlled, closed-loop manner that considers how the treatment is affecting the physiological characteristics of the clot and/or the treatment zone surrounding the clot.

In another mode of implementation the phase settings are adjusted based on the quality of the focus. The focal quality may be sensed using regular imaging or, in some cases, unique modes of imaging tailored to assess focus quality such as acoustic radiation force imaging. In these implementations, the phases are dithered to identify optimal focus that defines the phase setting.

While the invention has been particularly shown and described with reference to specific embodiments, it should be understood by those skilled in the area that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A system for delivering acoustic energy to a clot, the system comprising:
   a. a focused-ultrasound phased-array transducer;
   b. means for monitoring liquid content of the clot as ultrasound energy is directed at the clot; and
   c. a controller configured to automatically (i) operate the transducer, (ii) analyze the monitored liquid content, and (iii) adjust transducer operation based on the monitored liquid content.

2. The system of claim 1 wherein the means for monitoring liquid content comprise a visual display.

3. The system of claim 1 further comprising a processor for generating correction factors based on the liquefaction information and wherein the controller is responsive to the processor, thereby implementing the correction factors and influencing the application of acoustic energy to the clot.

4. A method for treating a clot, the method comprising the steps of:
   a. applying, focused ultrasound energy to the clot using a focused-ultrasound phased-array transducer;
   b. monitoring liquid content of the clot as ultrasound energy is directed at the blood vessel;
   c. automatically analyzing the monitored liquid content; and
   d. operating the transducer including adjusting transducer operation based on the monitored liquid content.

5. The method of claim 4 further comprising obtaining subsequent images of the clot during the application of the ultrasound energy.

6. The method of claim 5 further comprising generating respective correction factors for each transducer element of the transducer array based on the images.

* * * * *

UNITED STATES PATENT AND TRADEMARK OFFICE
CERTIFICATE OF CORRECTION

| | |
|---|---|
| PATENT NO. | : 8,425,424 B2 |
| APPLICATION NO. | : 12/620235 |
| DATED | : April 23, 2013 |
| INVENTOR(S) | : Eyal Zadicario et al. |

Page 1 of 1

It is certified that error appears in the above-identified patent and that said Letters Patent is hereby corrected as shown below:

Title Page,

Item (73) Assignee should read: Insightec Ltd., Tirat Carmel (IL)

Signed and Sealed this
Sixteenth Day of July, 2013

Teresa Stanek Rea
*Acting Director of the United States Patent and Trademark Office*